US009931517B2

(12) United States Patent
Bean (10) Patent No.: US 9,931,517 B2
(45) Date of Patent: Apr. 3, 2018

(54) MAGNETIC PAIN RELIEF ARRAY

(71) Applicant: Roy Franklin Bean, Austin, TX (US)

(72) Inventor: Roy Franklin Bean, Austin, TX (US)

(73) Assignee: JRB ENTERPRIZES, Austin, TX (US)

(*) Notice: Subject to any disclaimer, the term of this patent is extended or adjusted under 35 U.S.C. 154(b) by 0 days.

(21) Appl. No.: 14/735,754

(22) Filed: Jun. 10, 2015

(65) Prior Publication Data

US 2016/0361560 A1 Dec. 15, 2016

(51) Int. Cl.
*A61N 2/00* (2006.01)
*A61N 2/06* (2006.01)

(52) U.S. Cl.
CPC ............ *A61N 2/008* (2013.01); *A61N 2/06* (2013.01)

(58) Field of Classification Search
CPC ............ A61N 2/06; A61N 2/006; A61N 2/02
See application file for complete search history.

(56) References Cited

U.S. PATENT DOCUMENTS

| 5,312,321 | A | | 5/1994 | Holcomb | |
|---|---|---|---|---|---|
| 5,984,854 | A | * | 11/1999 | Ishikawa | A61N 2/02 600/9 |
| 6,015,377 | A | * | 1/2000 | Brown | A61N 2/06 600/9 |
| 6,245,006 | B1 | | 6/2001 | Olson | |
| 6,461,288 | B1 | | 10/2002 | Holcomb | |
| 2007/0179333 | A1 | * | 8/2007 | Bove | A61N 2/06 600/15 |
| 2007/0260107 | A1 | * | 11/2007 | Mishelevich | A61N 2/004 600/14 |
| 2008/0103350 | A1 | * | 5/2008 | Farone | A61N 2/006 600/13 |

OTHER PUBLICATIONS

International Search Report for PCT/US2016/036227 dated Sep. 29, 2016.

* cited by examiner

*Primary Examiner* — Christine H Matthews
(74) *Attorney, Agent, or Firm* — King & Spalding LLP (57) ABSTRACT

A device used for relieving pain is disclosed herein. The device can include a base comprising a number of mounting surfaces. The device can also include a number of magnets disposed on the mounting surfaces, where each magnet includes a first end and a second end, where the first end has a first polarity, where the second end has a second polarity, and where the first polarity attracts the second polarity to create a magnetic field, and where the magnets create a number of magnetic fields that intersect at a target area.

18 Claims, 10 Drawing Sheets

MAGNETIC PAIN RELIEF ARRAY

TECHNICAL FIELD

Example embodiments described herein are generally related to devices for relieving pain, and in particular, methods, devices, and systems for relieving pain using magnetic arrays.

BACKGROUND

People of any age, gender, and race experience any of a number of types of pain at various times. Sometimes, this pain is chronic, occurring regularly, and other times this pain is temporary and occurs randomly. In the United States and a number of other countries, a common remedy for relieving pain is medicine. Some medicine can be bought over-the-counter (without a prescription), but such medicine is generally not very strong and so cannot effectively treat more acute pain. Other medicine can only be bought legally with a doctor's prescription. While prescription medicine can effectively treat acute pain, many prescription drugs can have adverse side effects, such as causing addiction and/or damaging an organ.

SUMMARY

In general, in one aspect, the disclosure relates to a device used for relieving pain. The device can include a body having at least one mounting surface. The device can also include a number of magnets disposed on the at least one mounting surface, where each magnet has a first end and a second end, where the first end has a first polarity, where the second end has a second polarity, where the first polarity attracts the second polarity, and where the plurality of magnets create a plurality of magnetic fields that intersect at a first target area.

In another aspect, the disclosure can generally relate a method for relieving pain in a portion of a body. The method can include providing a device, where the device includes a number of magnets mounted on at least one mounting surface of the device, where each magnet has a first end and a second end, where the first end has a first polarity, where the second end has a second polarity, and where the first polarity attracts the second polarity. The method can also include placing the device at a location proximate to the portion of the body, where the magnets generate a number of magnetic fields, where the magnetic fields intersect in a target area, and where the portion of the body is disposed in the target area. The method can further include removing, after a period of time, the device from the location proximate to the portion of the body.

These and other aspects, objects, features, and embodiments will be apparent from the following description and the appended claims.

BRIEF DESCRIPTION OF THE DRAWINGS

The drawings illustrate only example embodiments of magnetic pain relief devices and are therefore not to be considered limiting of its scope, as magnetic pain relief devices may admit to other equally effective embodiments. The elements and features shown in the drawings are not necessarily to scale, emphasis instead being placed upon clearly illustrating the principles of the example embodiments. Additionally, certain dimensions or positionings may be exaggerated to help visually convey such principles. In the drawings, reference numerals designate like or corresponding, but not necessarily identical, elements.

DETAILED DESCRIPTION OF EXAMPLE EMBODIMENTS

The example embodiments discussed herein are directed to systems, apparatuses, and methods of magnetic pain relief devices that include a magnet array (also sometimes called a plurality of magnets herein). While the example magnetic pain relief devices that include a magnet array shown in the Figures and described herein are directed to relieving pain, example embodiments also can be used for other purposes. An example of such other purposes can include, but are not limited to, improved blood circulation.

Example embodiments described herein use a magnetic field generated by each magnet. When multiple magnets (a magnet array) are used in conjunction with each other, the resulting magnetic fields can be combined to provide pain relieving effects when an area of pain is disposed within the magnetic field. A user as described herein may be any person that interacts with an example magnetic pain relief device. Examples of a user may include, but are not limited to, a patient, a physician, a nurse, a physical therapist, a caregiver, a company representative, a consultant, a contractor, and a manufacturer's representative.

The magnetic pain relief devices (or components thereof) described herein can be made of one or more of a number of suitable materials to allow the magnetic pain relief devices to meet certain standards and/or regulations while also maintaining durability in light of the one or more conditions under which the magnetic pain relief devices can be exposed. Examples of such materials can include, but are not limited to, aluminum, stainless steel, fiberglass, glass, plastic, ceramic, and rubber.

Example magnetic pain relief devices, or portions thereof, described herein can be made from a single piece (as from a mold, injection mold, die cast, or extrusion process). In addition, or in the alternative, example magnetic pain relief devices can be made from multiple pieces that are mechanically coupled to each other. In such a case, the multiple pieces can be mechanically coupled to each other using one or more of a number of coupling methods, including but not limited to epoxy, welding, fastening devices, compression fittings, mating threads, and slotted fittings. One or more pieces that are mechanically coupled to each other can be coupled to each other in one or more of a number of ways, including but not limited to fixedly, hingedly, removeably, slidably, and threadably.

Components and/or features described herein can include elements that are described as coupling, mounting, fastening, securing, or other similar terms. Such terms are merely meant to distinguish various elements and/or features within a component or device and are not meant to limit the capability or function of that particular element and/or feature. For example, a feature described as a "coupling feature" can couple, mount, secure, fasten, and/or perform other functions aside from merely coupling.

A coupling feature (including a complementary coupling feature) as described herein can allow one or more components and/or portions of an example magnetic pain relief device (e.g., a portion of a magnet platform) to become mechanically coupled, directly or indirectly, to another portion (e.g., another portion of a magnetic platform) of a pain relief device. A coupling feature can include, but is not limited to, a portion of a hinge, an aperture, a recessed area, a protrusion, a clamp, a slot, a spring clip, a tab, a detent, and mating threads. One component of an example magnetic pain relief device can be coupled to another component of the magnetic pain relief device by the direct use of one or more coupling features.

In addition, or in the alternative, a component of an example magnetic pain relief device can be coupled to another component of the magnetic pain relief device using one or more independent devices that interact with one or more coupling features disposed on a component of the magnetic pain relief device. Examples of such devices can include, but are not limited to, a pin, a hinge, a fastening device (e.g., a bolt, a screw, a rivet), and a spring. One coupling feature described herein can be the same as, or different than, one or more other coupling features described herein. A complementary coupling feature as described herein can be a coupling feature that mechanically couples, directly or indirectly, with another coupling feature.

Further, if a component of a figure is described but not expressly shown or labeled in that figure, the label used for a corresponding component in another figure can be inferred to that component. Conversely, if a component in a figure is labeled but not described, the description for such component can be substantially the same as the description for the corresponding component in another figure. The numbering scheme for the various components in the figures herein is such that each component is a three or four digit number and corresponding components in other figures have the identical last two digits.

In the foregoing figures showing example embodiments of magnetic pain relief devices that include a magnet array, one or more of the components shown may be omitted, repeated, and/or substituted. Accordingly, example embodiments of magnetic pain relief devices that include a magnet array should not be considered limited to the specific arrangements of components shown in any of the figures. For example, features shown in one or more figures or described with respect to one embodiment can be applied to another embodiment associated with a different figure or description.

In certain example embodiments, magnetic pain relief devices that include a magnet array are subject to meeting certain standards and/or requirements. For example, the American Medical Association (AMA) sets standards as to devices used in medical applications. Use of example embodiments described herein can meet such standards when required. In some applications, additional standards particular to that application may be met by example magnetic pain relief devices that include a magnet array.

Example embodiments of magnetic pain relief devices that include a magnet array will be described more fully hereinafter with reference to the accompanying drawings, in which example embodiments of magnetic pain relief devices that include a magnet array are shown. Magnetic pain relief devices that include a magnet array may, however, be embodied in many different forms and should not be construed as limited to the example embodiments set forth herein. Rather, these example embodiments are provided so that this disclosure will be thorough and complete, and will fully convey the scope of magnetic pain relief devices that include a magnet array to those of ordinary skill in the art. Like, but not necessarily the same, elements (also sometimes called components) in the various figures are denoted by like reference numerals for consistency.

Terms such as "first", "second", "third", "end", "outer", "top", "bottom", and "side" are used merely to distinguish one component (or part of a component or state of a component) from another. Such terms are not meant to denote a preference or a particular orientation. Also, the names given to various components described herein are descriptive of example embodiments and are not meant to be limiting in any way. Those of ordinary skill in the art will appreciate that a feature and/or component shown and/or described in one embodiment (e.g., in a figure) herein can be used in another embodiment (e.g., in any other figure) herein, even if not expressly shown and/or described in such other embodiment. For each of the figures described below, one or more of the features shown in a figure may be omitted, added, repeated, and/or substituted. Accordingly, embodiments shown in such figure should not be considered limited to the specific arrangements of components shown in such figure.

Figure 1:
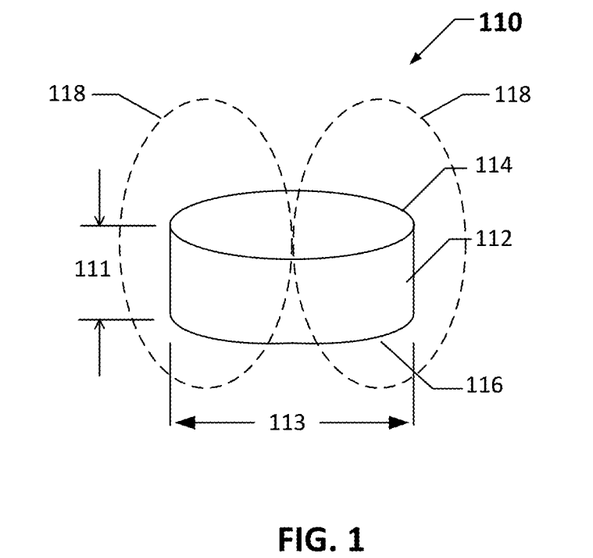
FIG. 1 shows a magnet in accordance with certain example embodiments.

FIG. 1 shows a magnet 110 in accordance with certain example embodiments. The magnet 110 can have any of a number of shapes and/or sizes. For example, as shown in FIG. 1, the magnet 110 can have a cylindrical shape with a height 111 (e.g., ¾ inches) and a diameter 113 (e.g., 1¾ inches). In such a case, the magnet 110 can have a top 114, a bottom, 116, and a side 112 disposed between the top 114 and the bottom 116. The top 114 and the bottom 116 of the magnet 110 can also be called ends or poles of the magnet 110. The magnet 110 can be made of one or more of a number of materials, at least one of which has magnetic properties. Examples of such materials can include, but are not limited to, ferrite oxide, iron, nickel, cobalt, lodestone, and alnico.

The top 114 and the bottom 116 of the magnet can each have a polarity. Characteristic of magnets, polarity (e.g., positive polarity) of the top 114 of the magnet 110 can be opposite the polarity (e.g., negative polarity) of the bottom 116 of the magnet 110, where one polarity attracts the opposite polarity. In this way, a magnetic field 118 is formed, traveling directionally from one polarity to the opposite polarity. The strength and shape of the magnetic field 118 can vary based on a number of factors. Such factors can include, but are not limited to, the material (e.g., ferrite oxide) of the magnet 110, the height 111 of the magnet 110, the diameter 113 of the magnet 110, the shape of the magnet 110, and other magnetic forces that are proximate to the magnet 110.

The top 114 and the bottom 116 of the magnet 110 can each have a surface. The surface of the top 114 and the surface of the bottom 116 can have one or more of any number of features. Examples of such features can include, but are not limited to, flat, smooth, textured, and curved. The surface of the top 114 and the surface of the bottom 116 can be substantially parallel to each other. Alternatively, the surface of the top 114 and the surface of the bottom 116 can be antiparallel to each other, offset by some acute angle.

Figure 2A:
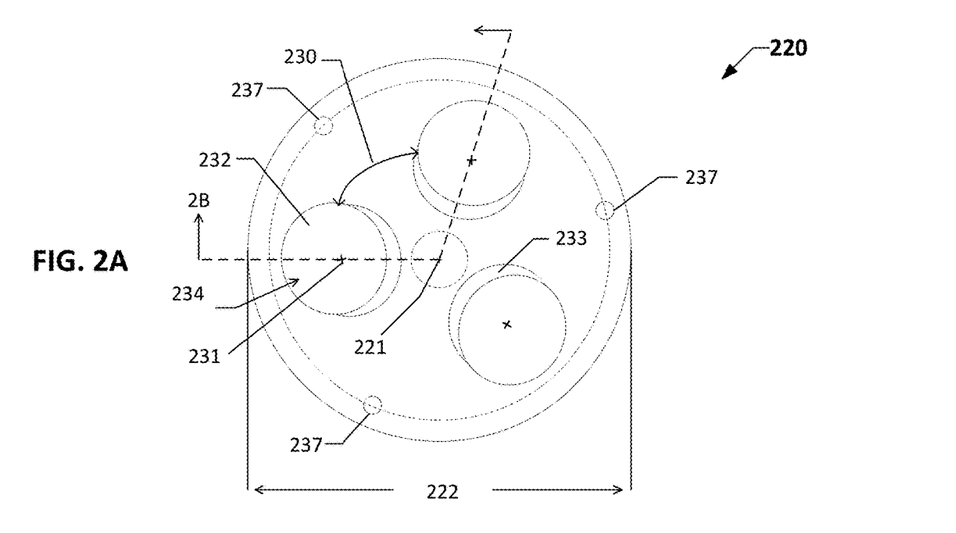
FIGS. 2A and 2B show a base of a magnet platform in accordance with certain example embodiments.
Figure 2B:
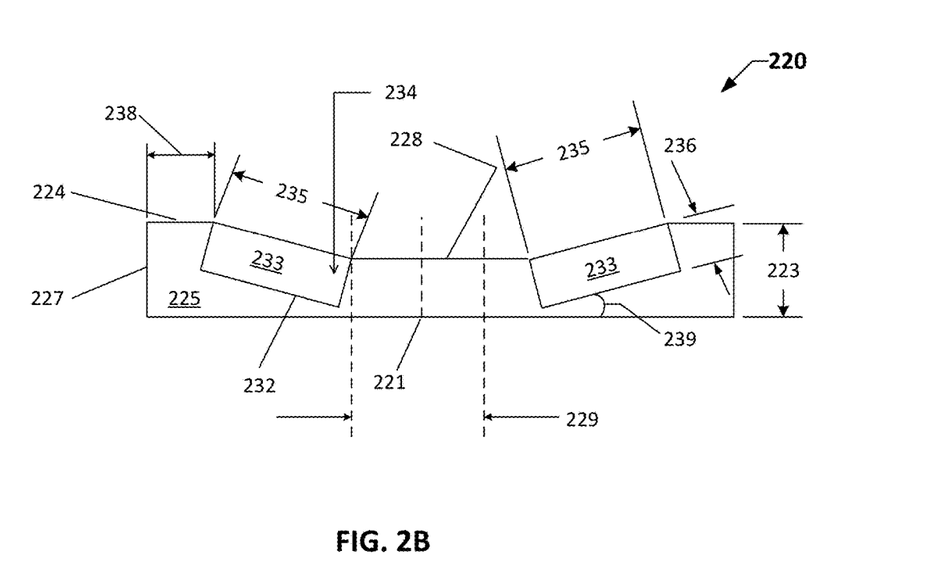

In certain example embodiments, multiple magnets are used in one device. The magnets can be mounted to a body of an example device in one or more of a number of ways. For example, one or more magnets can be mounted directly to the body. As another example, one or more magnets can be encased in one or more magnet platforms. A magnet platform can be one piece or multiple pieces. In addition, or in the alternative, a magnet platform (or portions thereof) can have any of a number of shapes, sizes, and configurations (e.g., number of magnets encased in a magnet platform). FIGS. 2A and 2B show a top view and a cross-sectional side view, respectively, of a base 220 of a magnet platform in accordance with certain example embodiments.

Referring to FIGS. 1-2B, the base 220 of the magnet platform of FIGS. 2A and 2B is substantially cylindrical in shape, with a substantially round shape when viewed from above, as in FIG. 2A. The base 220 can have an overall diameter 222 (defined by the outer side 227 of the base 220) and an overall height 223 (defined by the top outer surface 224 and the bottom surface 226 of the base 220). The base 220 can have one or more magnet receivers 230, where each magnet receiver 230 can receive at least one magnet 110. In this case, each magnet receiver 230 is configured to receive one magnet 110, and there are three magnet receivers 230 that are disposed substantially equidistant from the center 221 of the base 220 when viewed from above. The magnet receivers 230 alternatively can be disposed in some other orientation (e.g., randomly) with respect to the center 221 of the base 220. Here, the magnet receivers 230 are separated by a distance 229.

The magnet receivers 230 of the base 220 can be substantially the same (e.g., in terms of height 236, diameter 235, shape) as, or different than, each other. In this case, the three magnet receivers 220 are substantially the same as each other. Further, each magnet receiver 230 can be set at some angle 239 relative to a horizontal basis (in this case, as represented by the top outer surface 224, the top middle surface 228, and the bottom surface 226 of the base 220). In some cases, the angle 239 is zero. Alternatively, as shown in FIGS. 2A and 2B, the angle 239 is non-zero. For example, the angle 239 can be 4°. When the angle 239 is zero, the top middle surface 228 is substantially planar with the top outer surface 224. Alternatively, when the angle 239 is acute and positive (non-zero), the top middle surface 228 is recessed in the base 230 relative to the top outer surface 224.

When the angle 239 is non-zero, and when the surface of the top 114 and the surface of the bottom 116 of the magnet 110 are substantially parallel with each other, the magnetic fields of the magnets 110 disposed in the magnet receivers 230 can be targeted to intersect some area (sometimes called an area of treatment) located above and/or below the magnets 110 (which is also above and/or below the base 220 of the magnet platform). Similarly, when the angle 239 is zero, and when the surface of the top 114 and the surface of the bottom 116 of the magnet 110 form an acute angle with respect to each other, the magnetic fields of the magnets 110 disposed in the magnet receivers 230 can be targeted to intersect some area located above the magnets 110.

When the angle 239 of each magnet receiver 230 is substantially the same, and when the shape of each magnet 110 is substantially the same, the area of treatment that the magnetic fields generated by the magnets 110 is targeted to intersect is located above the top middle surface 228 of the base 220. An example of how the magnetic fields of magnets can be targeted to an area of treatment is shown below with respect to FIG. 5.

In certain example embodiments, each magnet receiver 230 has at least one side wall 233 and a bottom wall 232 that forms a cavity 234 in the body 225 of the base 225 and into which a magnet 110 is disposed. Each magnet receiver 230 can have a diameter 235 (or a width if the cross-sectional shape of the magnet receiver 230 when viewed from above is not circular) and a height 236 (also called a depth 236). The shape and size of the magnet receiver 230 can be substantially the same as, or slightly larger than, the shape and size of the magnet 110 that is disposed within the magnet receiver 230.

Figure 3A:
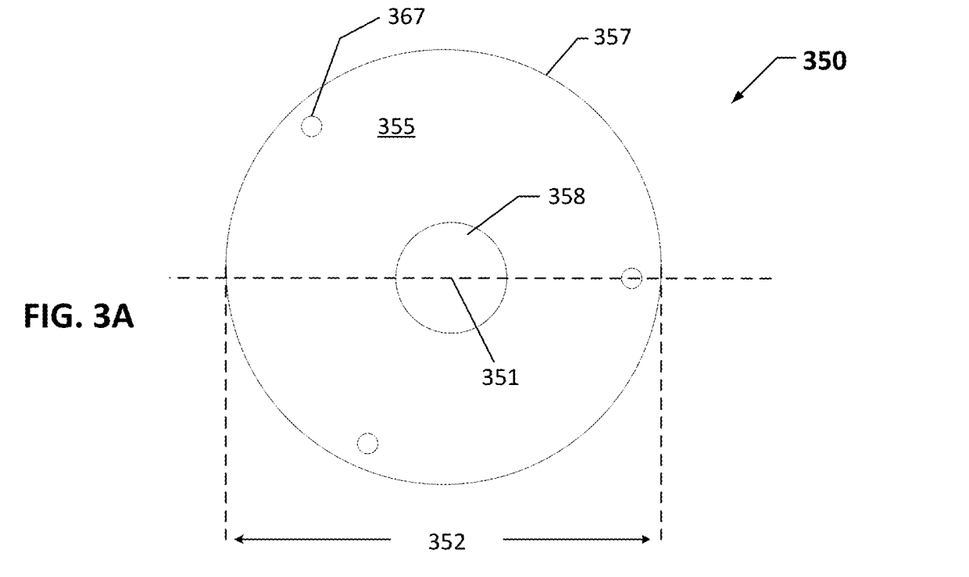
FIGS. 3A and 3B show a cover of a magnet platform in accordance with certain example embodiments.
Figure 3B:
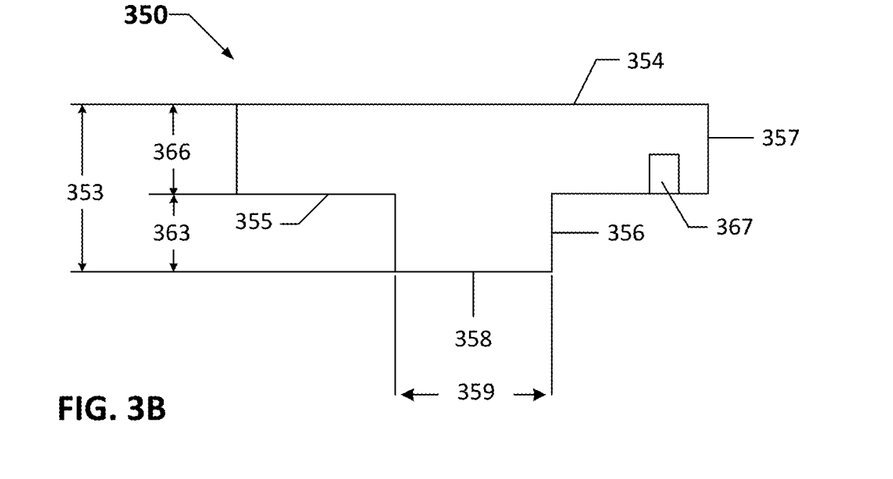

A magnet receiver 230 can include one or more coupling features (e.g., mating threads, threaded apertures, detents) that complement a coupling feature of a magnet 110 disposed within the magnet receiver 230. Alternatively, the magnet platform can include a cover that couples to the base 230 and thus retains the magnets 110. In such a case, the base 220 can include one or more coupling features that allow the base 220 to couple to the cover. For example, as shown in FIG. 2A, the base 220 can include threaded apertures 237 that coincide with a coupling feature (e.g., threaded apertures) of the cover. FIGS. 3A and 3B shows a cover 350 of a magnet platform in accordance with certain example embodiments.

Referring to FIGS. 1-3B, the cover 350 of the magnet platform of FIGS. 3A and 3B is substantially cylindrical in shape, with a substantially round shape when viewed from below, as in FIG. 3A. The cover 350 can have an overall diameter 352 and an overall height 353. The diameter 352 of the cover 350 (or a width 352 if the cover is not circular when viewed cross-sectionally from above) can be substantially the same as the diameter 222 of the base 220. The cover 350 can have one or more magnet receivers (not shown), where each magnet receiver can receive the top end of at least one magnet 110. Alternatively, as in this case, if the magnet 110 is disposed completely within the magnet receiver 230 of the base 220, the cover 350 does not have a magnet receiver.

In certain example embodiments, the cover 350 has a body 362 defined by at least one top side wall 357, at least one bottom side wall 356, a top wall 354, an upper bottom wall 355, and a lower bottom wall 358. If a magnet 110 extends beyond the height of a magnet receiver 230, the cover 350 can have one or more features (e.g., recesses) in the upper bottom wall 355. The cover 350 can have multiple portions. In this case, the cover 350 has an upper portion and a lower portion, where the upper portion has a diameter 352 (or a width if the cross-sectional shape of the cover 350 when viewed from above is not circular) and a height 366 (also called a depth), and where the lower portion has a diameter 358 and a height 363. The cover 350 has an overall height 353.

The shape and size of the cover 350 (including the upper portion and the lower portion) can vary so that, when the cover 350 is coupled to the base 220, the magnets 110 are completely or partially disposed in the magnet platform. The cover 350 can have one or more coupling features (in this case, threaded apertures) that complement any coupling features of the base 220 to allow the base 220 and the cover 350 to couple to each other, either directly or indirectly.

Figure 4A:
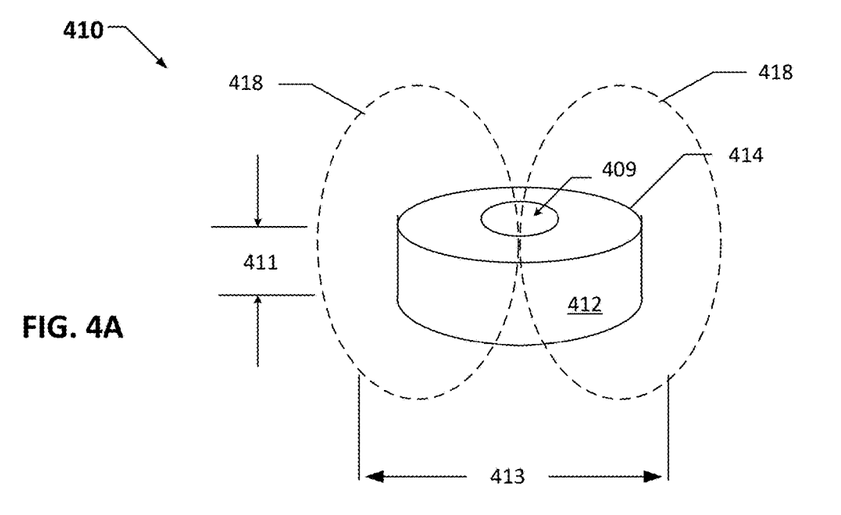
FIGS. 4A and 4B show an alternative magnet in accordance with certain example embodiments.
Figure 4B:
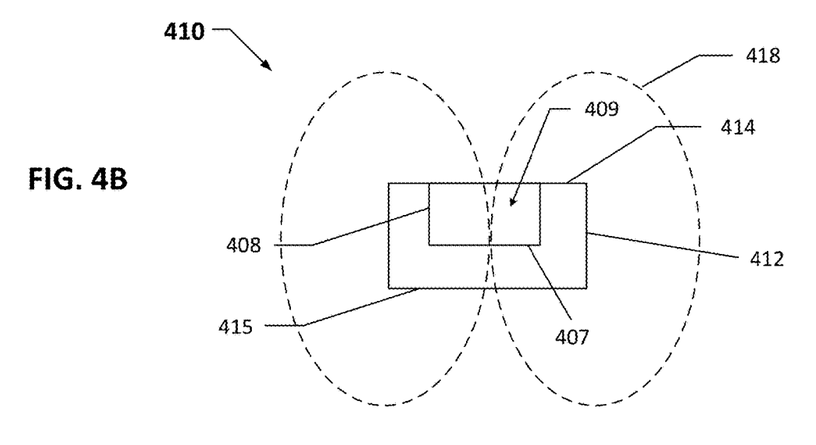

FIGS. 4A and 4B show a top-side perspective view and a cross-sectional side view, respectively, of an alternative magnet 410 in accordance with certain example embodiments. The magnet 410 of FIGS. 4A and 4B can be substantially the same as the magnet 110 of FIG. 1, except as described below. Specifically, at least one of the poles (in this case the top end 414) of the magnet 410 has a cavity (hidden from view), defined by a bottom wall 407 (having a diameter or length of, for example, ¾ inches) and at least one side wall 408 (having a height of, for example, ¾ inches). The cavity can be used to hold a mineral core 409 having substantially the same size as, or a slightly smaller size than, the cavity. The mineral core 409 can be considered part of, or a separate component from, the magnet 410.

In certain example embodiments, the mineral core 409 is used to adjust or alter the magnetic waves 418 generated by the magnet 410. The mineral core 409 can be any one or more of a number of minerals. Examples of such minerals can include, but are not limited to, calcium, magnesium, iron, zinc, and tin. A mineral can be found naturally or generated through some process. In some cases, the mineral core 409 may include, in whole or in part, an element or compound that is not a mineral. Examples of non-mineral components of a mineral core 409 can include, but are not limited to, tree bark, herbs, spices, plants, and roots. The mineral core 409 can be removable and/or replaceable by a user. The mineral core 409 (including components thereof) can have one or more of a number of forms. Examples of such forms can include, but are not limited to, a solid, a gel, a liquid, and a powder.

When the mineral core 409 is solid or semi-solid, the mineral core 409 can include one or more coupling features (e.g., mating threads disposed on the outer surface of the mineral core 409) that complement one or more coupling features disposed in the cavity. In addition, or in the alternative, as when the mineral core 409 has certain forms (e.g., powder, liquid), the top end 414 of the magnet 410 can have one or more features (e.g., a removable cap, a slidable cover) that encloses the cavity and helps to retain the mineral core 409 within the cavity.

Figure 5:
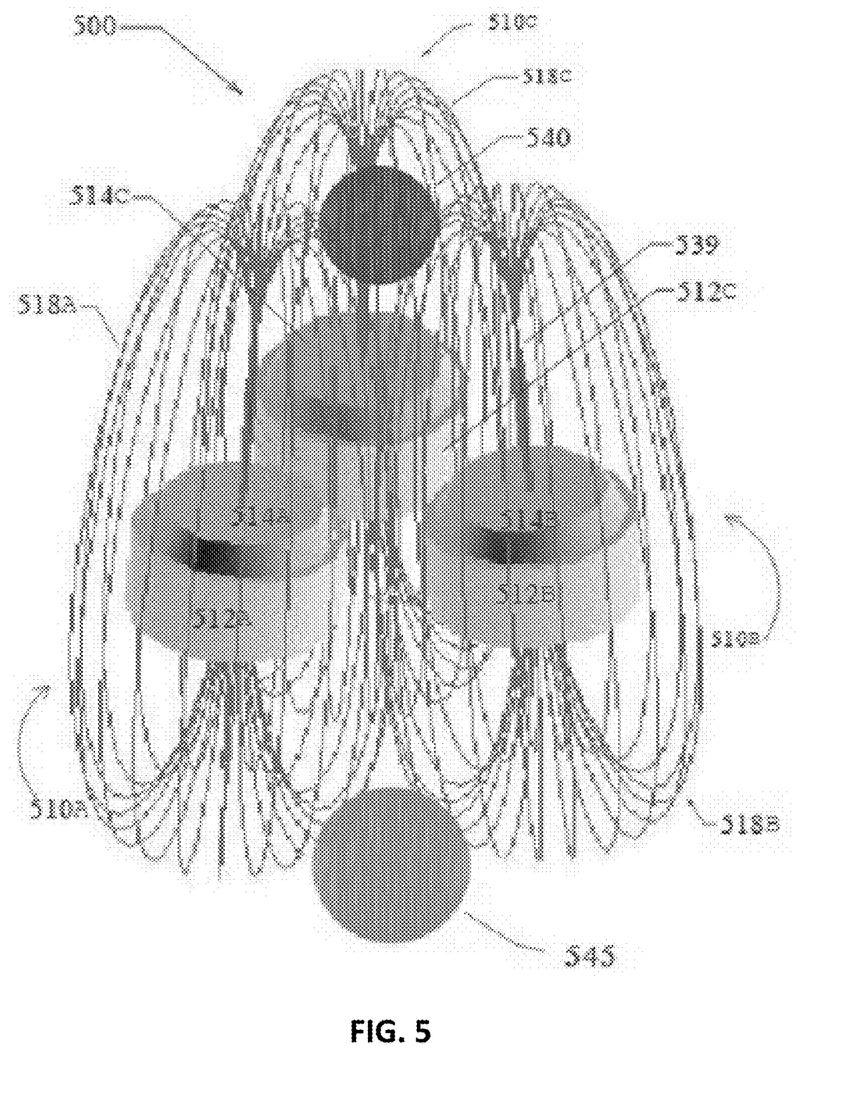
FIG. 5 shows a trio of magnets in accordance with certain example embodiments.

FIG. 5 shows a magnet array 500 that includes multiple magnets 510 positioned in proximity to each other in accordance with certain example embodiments. In this case, there are three magnets (magnet 510A, magnet 510B, magnet 510C) in the magnet array 500. Each magnet 510 of FIG. 5 can be substantially similar to magnet 110 of FIG. 1 (without a mineral core) or magnet 410 of FIG. 4 (with a mineral core). Each magnet 510 creates its own magnetic field 518 that flows from one pole (e.g., top end 514) to the opposite pole (hidden from view). When the three magnets 510 are positioned proximate to each other, the magnetic fields 518 can overlap in one or more areas, shown as target area 540 and target area 545 in FIG. 5. While called an "area", the target area 540 and the target area 545 can each actually be a volume of space, defined within three dimensions.

When the magnets 510 of FIG. 5 are oriented such that the positive polarity is directed upward and the negative polarity is directed downward, then target area 540 accumulates protons from the overlap of the magnetic fields 518, and target area 545 accumulates electrons from the overlap of the magnetic fields 518. When the magnets 510 of FIG. 5 are oriented such that the negative polarity is directed upward and the positive polarity is directed downward, then target area 540 accumulates electrons from the overlap of the magnetic fields 518, and target area 545 accumulates protons from the overlap of the magnetic fields 518.

The overlap of the magnetic fields, represented by target area 540 above the magnets 510 and by target area 545 below the magnets 510, created by the magnet array 500 draws one or more electrical elements (e.g., soft electrons, protons) from the surrounding atmosphere into the respective target area. Each target area of the magnetic fields 518 can be manipulated by adding and/or changing the mineral core of one or more magnets 510 and/or by changing the position (e.g., location, angle) of one or more magnets 510 in the magnet array 500. For example, when the magnets 510 are arranged to form a substantially equidistant triangular shape, with the top end 514 (e.g., positive pole) of each magnet 510 tilted towards the center at some angle 539, the resulting target area 540 of the magnetic fields 518 can cause a "pinching" effect that produces a cloud of protons to hover some distance (e.g., an inch) above the top end 514 of the magnets 510. By tilting the magnets 510 toward each other, as shown in FIG. 5, the characteristics (e.g., intensity, size) of target area 540 can be different than the corresponding characteristics of target area 545.

As another example, by adding certain minerals and/or other elements (e.g., plants, roots) to the mineral core (e.g., mineral core 409), components of those minerals and/or other elements become part of the magnetic field 518 of its respective magnet 510. As a result, at least some of those components of those minerals and/or other elements can become suspended within a target area (e.g., target area 540). The properties of these minerals and/or other elements can help contribute to the pain relief induced by the magnetic fields 518 within the target area. One target area (e.g., target area 540) can suspend certain minerals and/or other elements (or portions thereof), while the other target area (e.g., target area 545) can suspend other minerals and/or other elements (or portions thereof). Thus, each target area of the same magnet array 500 can generate different results with respect to pain relief.

This "pinching" effect, particularly when the target area is enhanced by the presence of minerals and/or other elements, can result in one or more benefits when the target area (e.g., target area 540) is directed at a subcutaneous body area. Example of benefits that result from a target area of the magnetic fields 518 can include, but are not limited to, stimulating the structure and metabolism of subcutaneous tissue and blood in and around a target area, softening cell structure in and around a target area, increasing blood flow in and around a target area, reducing inflammation in and around a target area, relaxing muscles in and around a target area, encouraging blood flow in an area of bone/cartilage joint damage in and around a target area, and causing red blood cells to concentrate in and around a target area.

In certain example embodiments, a target area (e.g., target area 540, target area 545) can be applied to any part of the body. Similarly, by reversing the polarity of the magnets 510, the target area 545 can be applied to any part of the body. Alternatively, by using the opposite side of the device that holds the magnet array 500, the target area 545 can be applied to any part of the body. Examples of parts of the body that a target area can be applied to can include, but is not limited to, the ankle, the knee, the hip, the elbow, the wrist, the shoulder, the neck, the arm, the eye, and the leg. The body can be a human body or the body of an animal. Areas of the body to which a target area is applied, or even the body itself, should be free of devices (e.g., pacemakers) whose function can be affected by a magnetic field. Further, certain parts of the body that can become damaged from directed magnetic fields should not be placed in a target area. In addition, the amount of time that a target area is applied to a part of the body may need to be limited to avoid overstimulation of the part of the body, deficiencies in other (e.g., adjacent) parts of the body, and/or other adverse conditions.

In some cases, a user may reverse the polarity of the magnets 510 in the magnet array 500 to obtain a desired level of pain relief. For example, in warmer ambient temperatures (e.g., in the summer time), for the orientation of the magnets 510 shown in FIG. 5 (with the top end 514 of each magnet 510 having a positive polarity), target area 540 can provide more effective pain relief relative to the amount of pain relief provided by target area 545. Conversely, in cooler ambient temperatures (e.g., in the winter time), target area 545 can provide more effective pain relief relative to the amount of pain relief provided by target area 540.

Figure 6:
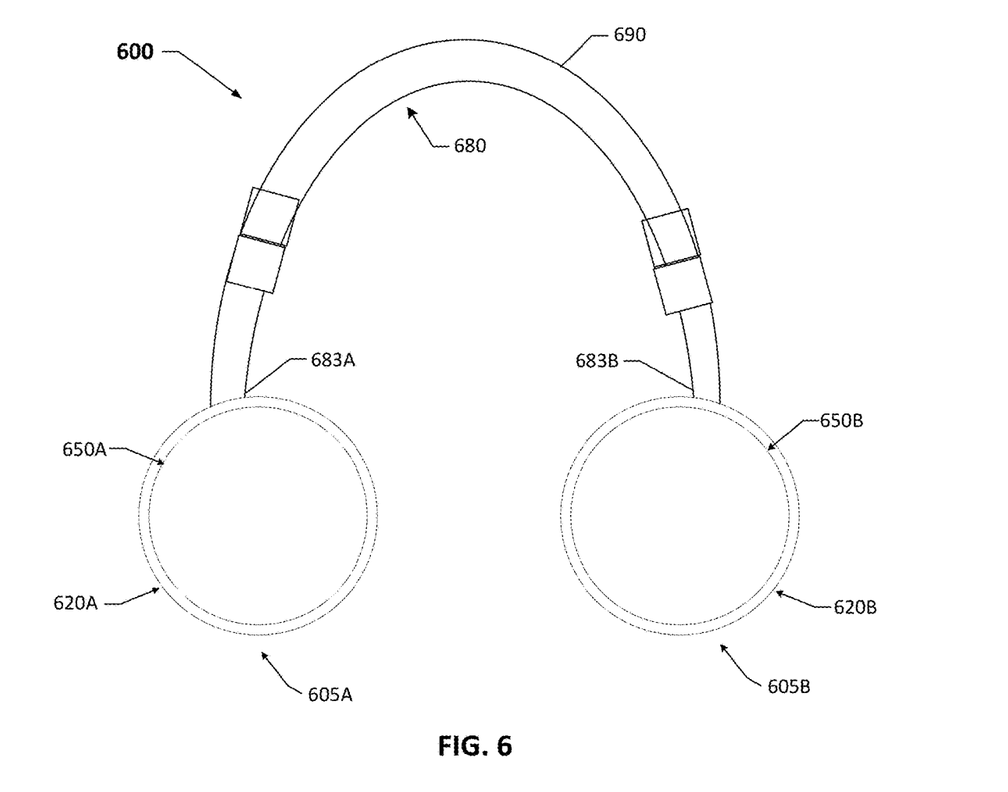
FIG. 6 shows a magnetic pain relief device in accordance with certain example embodiments.

FIG. 6 shows a magnetic pain relief device 600 in accordance with certain example embodiments. Referring to FIGS. 1-6, the device 600 includes a body 680 and two magnet platforms 605 (magnet platform 605A and magnet platform 605B). The body 680 is a flexible strap 690, where one end of the strap 690 is a mounting surface 683A that couples to one magnet platform (e.g., magnet platform 605A) and the other end of the strap 690 is a mounting surface 683B that couples to the other magnet platform (e.g., magnet platform 605B). The strap 690 can have any of a number of suitable characteristics (e.g., length, width, thickness, elasticity).

Each magnet platform 605 can include a base 620 and a cover 650, where the base 620 and the cover 650 can be substantially the same as the base 220 and the cover 350, respectively, described above. Each magnet platform 605 can house any number (e.g., one, three) of magnets (e.g., magnet 110, magnet 410). The base 620 and the cover 650 of each magnet platform 605 can be permanently or removably coupled to each other. Magnet platform 605A can be substantially the same as (e.g., in terms of size, shape, number of magnets 410), or different than, magnet platform 605B.

Figure 7:
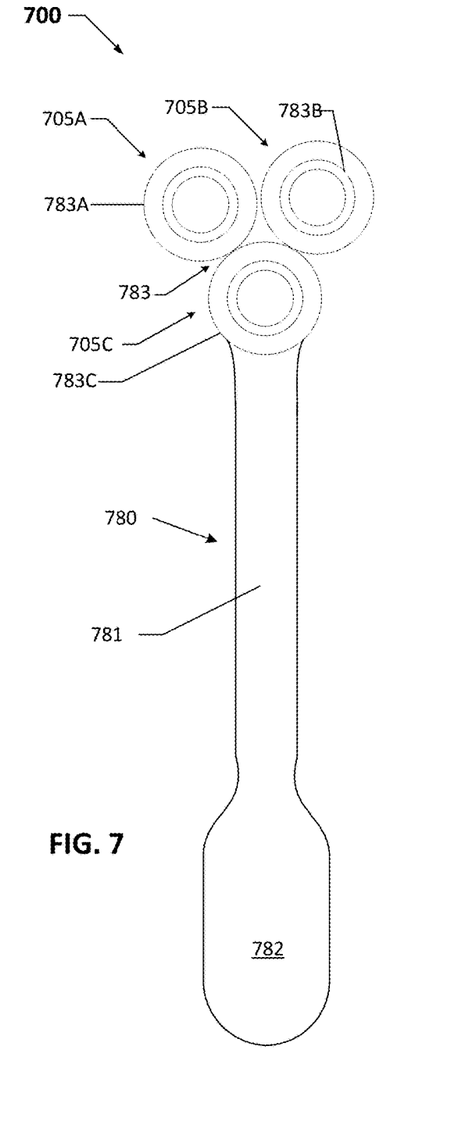
FIG. 7 shows another magnetic pain relief device in accordance with certain example embodiments.

FIG. 7 shows another magnetic pain relief device 700 in accordance with certain example embodiments. Referring to FIGS. 1-7, the device 700 includes a body 780 and three magnet platforms 705 (magnet platform 705A, magnet platform 705B, and magnet platform 705C). The body 780 of FIG. 7 includes a stem 781 with three mounting surfaces 783 (mounting surface 783A, mounting surface 783B, and mounting surface 783C) disposed at one end of the stem 781 and a handle 782 disposed at the other end of the stem 781.

The magnet platforms 705 can be substantially the same as the magnet platforms described above. For example, in this case, the each magnet platform 705 can encase a single magnet (e.g., magnet 410). In certain alternative embodiments, rather than magnet platforms 705, multiple magnets can be coupled directly to the mounting surfaces 783. In other words, the device 700 can be without magnet platforms 705 so that the magnets (hidden from view in FIG. 7) are directly exposed and accessible. In such a case, a user can more easily remove and/or change a mineral core in one or more of the magnets. Otherwise, when a magnet is encased in a magnet platform 705, the cover 750 of the magnet platform 705 must be removed in order for a user to access the magnet.

Figure 8:
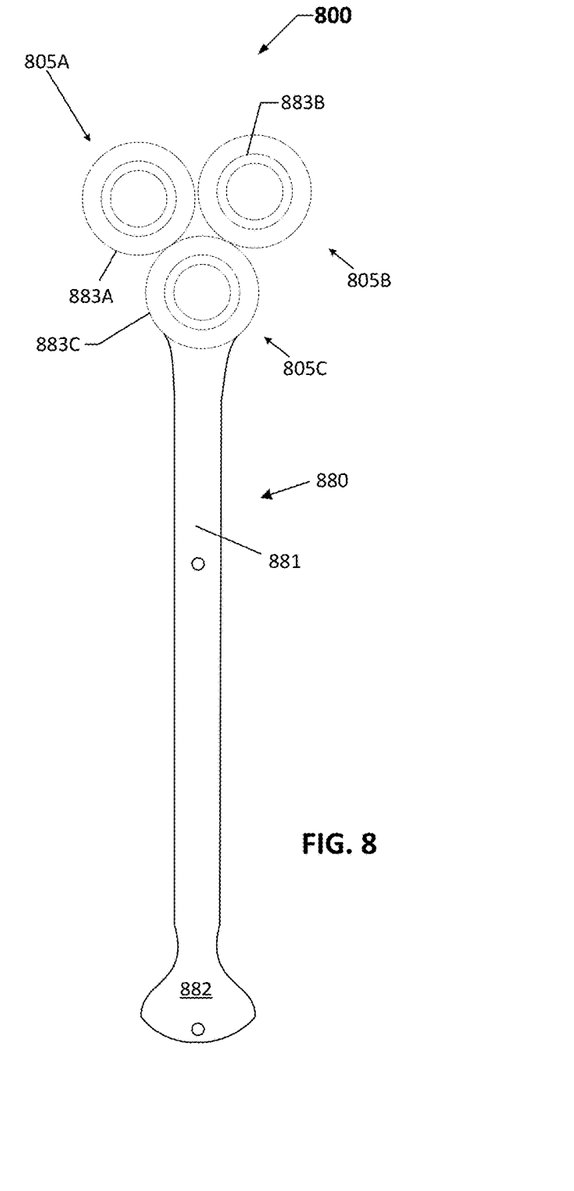
FIG. 8 shows yet another magnetic pain relief device in accordance with certain example embodiments.

FIG. 8 shows yet another magnetic pain relief device 800 in accordance with certain example embodiments. Referring to FIGS. 1-8, the device 800 includes a body 880 and three magnet platforms 805 (magnet platform 805A, magnet platform 805B, and magnet platform 805C). The device 800 of FIG. 8 is substantially the same as the device 700 of FIG. 7, except as described below. Specifically, the components (e.g., the stem 881, the handle 882, and the three mounting surfaces 883) of the body 880 of FIG. 8 are smaller and/or have different shapes compared to the corresponding components of the body 780 of FIG. 7. As a consequence, the magnet platforms 805 of FIG. 8 are spaced closer together compared to the spacing of the magnet platforms 705 of FIG. 7.

In addition, the magnets can be oriented along substantially the same plane. Alternatively, a magnet of the 800 device can be set on a plane that is acutely variant from the plane on which one or more other magnets of the device 800 are set. This can allow for creation of one or more target areas, as with target area 540 and target area 545 of FIG. 5. This can be accomplished in one or more of a number of ways. For example, the top end (e.g., top end 414) and the bottom end (e.g., bottom end 415) of a magnet can be antiparallel to each other. As another example, as shown in FIG. 2, a magnet receiver (e.g., magnet receiver 230) of a base (e.g., base 220) of a magnet platform (e.g., magnet platform 805) can form a non-zero angle 239 with a horizontal basis (e.g., the bottom surface 226 of the base 220). As yet another example, a mounting surface (e.g., mounting surface 783A, mounting surface 783B) of a device can be anti-planar with respect to one or more other mounting surfaces of the device.

Figure 9:
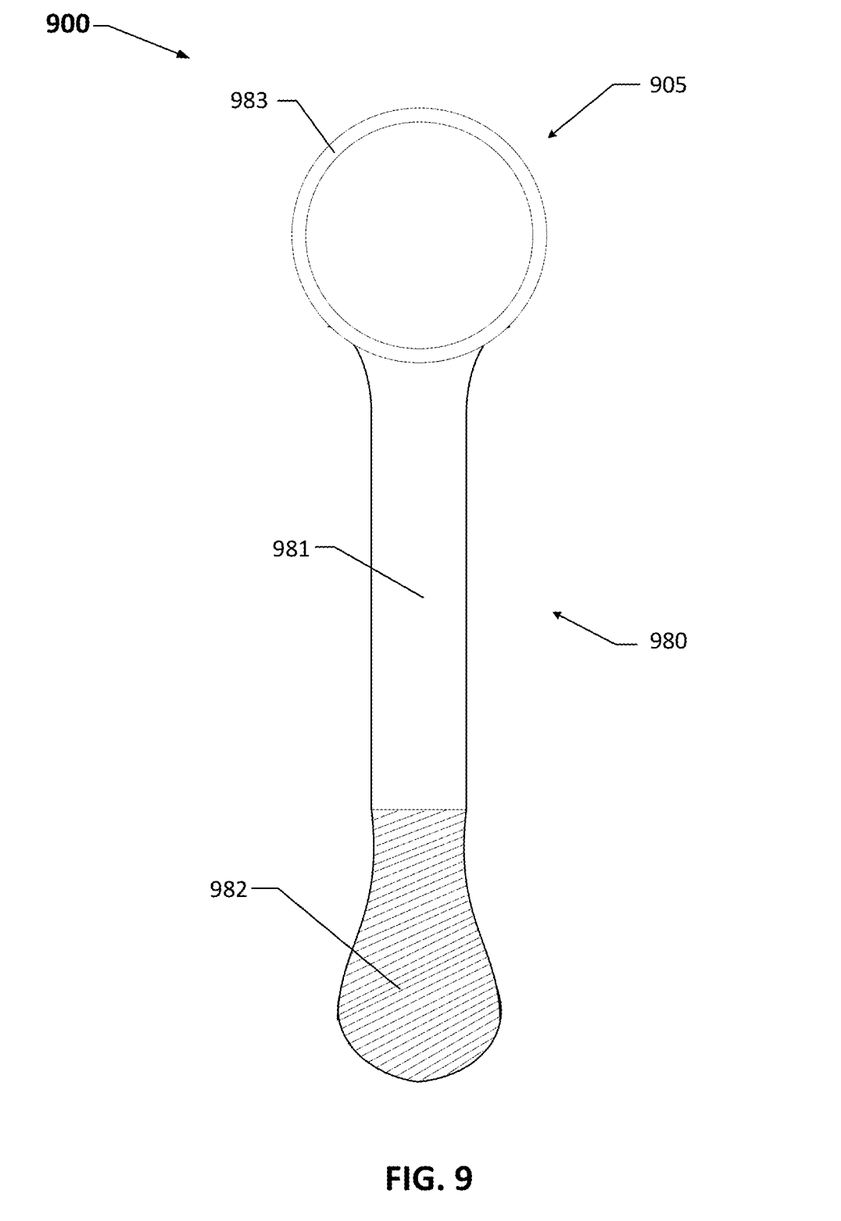
FIG. 9 shows still another magnetic pain relief device in accordance with certain example embodiments.

FIG. 9 shows still another magnetic pain relief device 900 in accordance with certain example embodiments. Referring to FIGS. 1-9, the device 900 includes a body 980 and a single magnet platform 905. The device 900 of FIG. 9 is substantially the same as the device 700 of FIG. 7 and the device 800 of FIG. 8, except as described below. Specifically, the mounting surface 983 of the body 980 is configured to host a single magnet platform 905, which in turn can have disposed thereon a magnet array, such as magnet array 500 of FIG. 5.

Figure 10A:
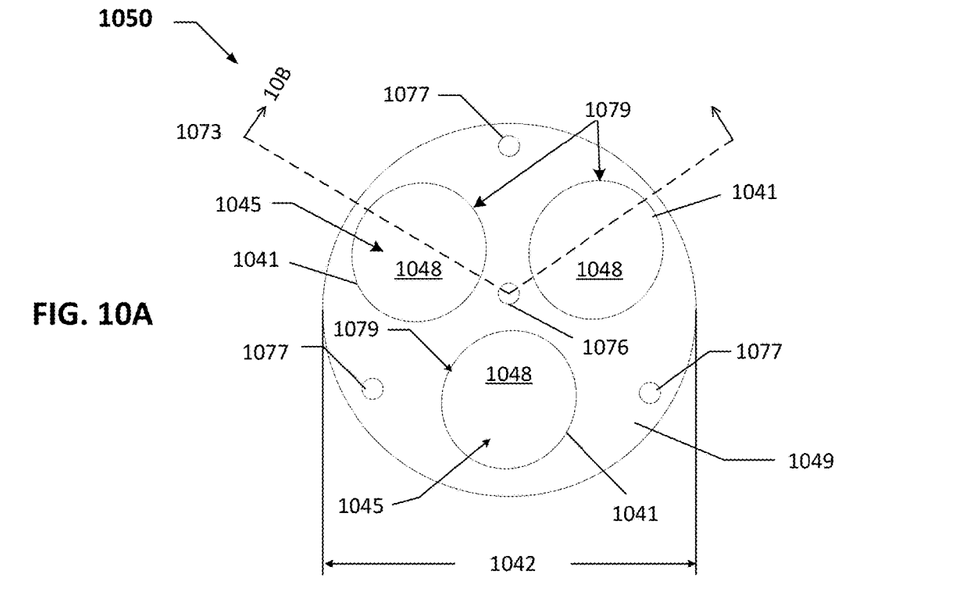
FIGS. 10A and 10B show another cover of a magnet platform in accordance with certain example embodiments.
Figure 10B:
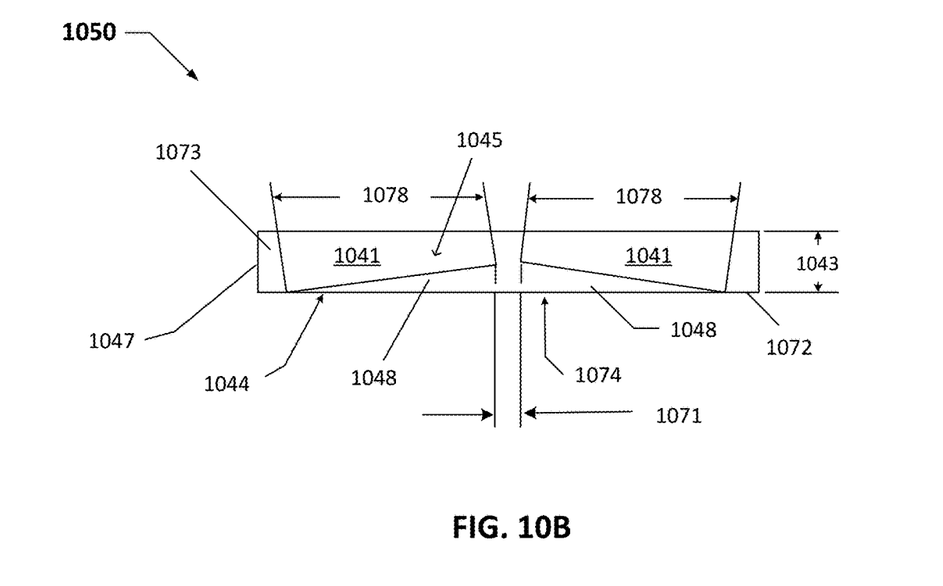

FIGS. 10A and 10B show another cover 1050 of a magnet platform in accordance with certain example embodiments. FIG. 10A shows a bottom view of the cover 1050, and FIG. 10B shows a cross sectional side view of the cover 1050. The cover 1050 of FIGS. 10A and 10B is an alternative to the cover 350 of FIGS. 3A and 3B. Referring to FIGS. 1-10B, the cover 1050 of the magnet platform of FIGS. 10A and 10B is substantially cylindrical in shape, with a substantially round shape when viewed from below, as in FIG. 10A. The cover 1050 can have an overall diameter 1042 (defined by the outer side 1047 of the cover 1050) and an overall height 1043 (defined by the top surface 1049 and the bottom surface 1072 of the cover 1050). The diameter 1042 of the cover 1050 (or a width 1042 if the cover 1050 is not circular when viewed cross-sectionally from above) can be substantially the same as the diameter (e.g., diameter 222) of a base (e.g., base 220).

The cover 1050 can have one or more magnet receivers 1079, where each magnet receiver 1079 can receive the top end of at least one magnet (e.g., magnet 110). In this case, each magnet receiver 1079 is configured to receive one magnet, and there are three magnet receivers 1079 that are disposed substantially equidistant from the center 1076 of the cover 1050 when viewed from below. The magnet receivers 1079 alternatively can be disposed in some other orientation (e.g., randomly) with respect to the center 1076 of the cover 1050. In any case, the size, shape, and configuration of the magnet receivers 1079 can be configured to match those of a base (e.g., base 220) to which the cover 1050 couples. Here, the magnet receivers 1079 are separated by a distance 1071.

The magnet receivers 1079 of the cover 1050 can be substantially the same (e.g., in terms of height, diameter, shape) as, or different than, each other. In this case, the three magnet receivers 1079 are substantially the same as each other. Further, each magnet receiver 1079 can be set at some angle 1074 relative to a horizontal basis (in this case, as represented by the bottom surface 1044 and the top surface 1049 of the cover 1050). In some cases, the angle 1074 is zero. Alternatively, as shown in FIGS. 10A and 10B, the angle 1074 is non-zero. For example, the angle 1074 can be 4°. As another example, the angle 1074 can be substantially the same as the angle formed by the magnet receivers (e.g., magnet receivers 230) of the base (e.g., base 220) to which the cover 1050 couples.

When the angle 1074 is non-zero, and when the surface of the top 114 and the surface of the bottom 116 of the magnet 110 are substantially parallel with each other, the magnetic fields of the magnets 110 disposed in the magnet receivers 1079 can be targeted to intersect some area (sometimes called an area of treatment) located above and/or below the magnets 110 (which is also above and/or below the cover 1050 of the magnet platform).

Similarly, when the angle 1074 is zero, and when the surface of the top 114 and the surface of the bottom 116 of the magnet 110 form an obtuse angle with respect to each other in the cover 1050, the magnetic fields of the magnets 110 disposed in the magnet receivers 1079 can be targeted to intersect some other area located above and/or below the magnets 110. When the angle 1074 of each magnet receiver 1079 is substantially the same, and when the shape of each magnet 110 is substantially the same, the area of treatment that the magnetic fields generated by the magnets 110 is targeted to intersect (the target area) is located above and below the middle 1076 of the cover 1050.

In certain example embodiments, each magnet receiver 1079 has at least one side wall 1041 and a bottom wall 1048 that forms a cavity 1045 in the body 1073 of the cover 1050 and into which a magnet 110 is disposed. Each magnet receiver 1079 can have a diameter 1078 (or a width if the cross-sectional shape of the magnet receiver 1079 when viewed from above is not circular) and a height (also called a depth), which in this case is substantially the same as, but slightly less than, the height 1043 of the cover 1050. The shape and size of the magnet receiver 1079 can be substantially the same as, or slightly larger than, the shape and size of the magnet 110 that is disposed within the magnet receiver 1079.

A magnet receiver 1079 can include one or more coupling features (e.g., mating threads, threaded apertures, detents) that complement a coupling feature of a magnet 110 disposed within the magnet receiver 1079. Alternatively, the magnet platform can include a base that couples to the cover 1050 and thus retains the magnets 110. In such a case, the cover 1050 can include one or more coupling features that allow the cover 1050 to couple to the base. For example, as shown in FIG. 10A, the cover 1050 can include threaded apertures 1077 that coincide with a coupling feature (e.g., threaded apertures) of the base.

Figure 11:
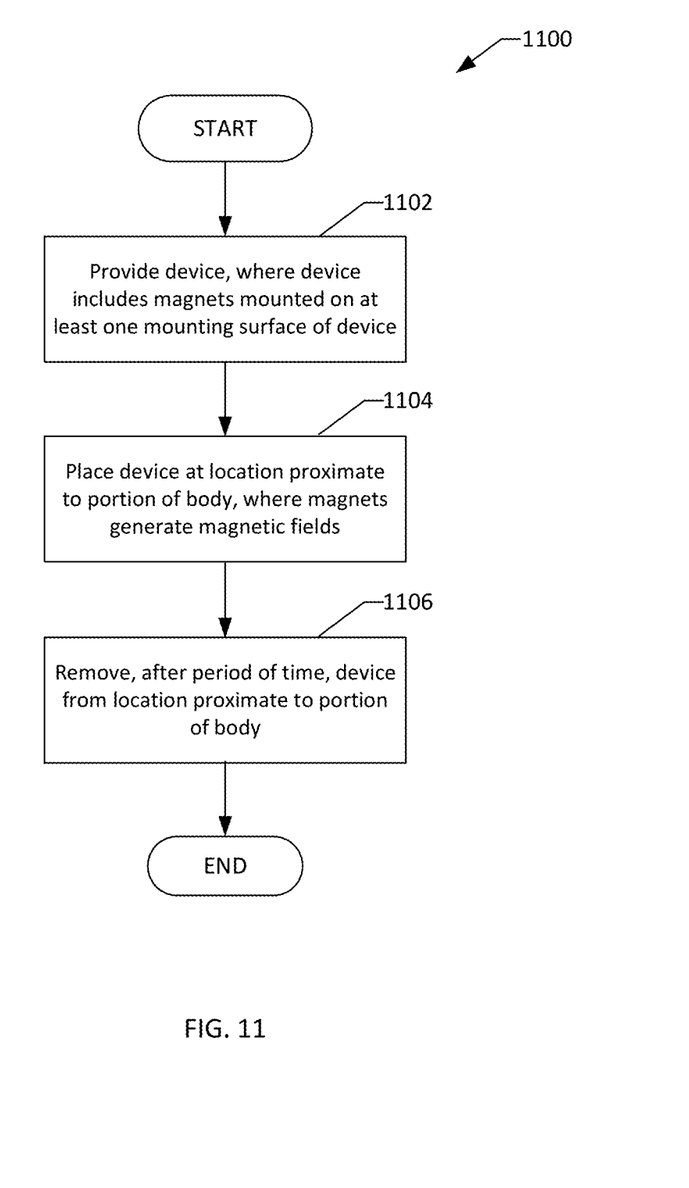
FIG. 11 shows a flowchart of a method for improving circulation in a portion of a body in accordance with certain example embodiments.

FIG. 11 shows a flowchart of a method 1100 for improving circulation in a portion of a body in accordance with certain example embodiments. While the various steps in this flowchart are presented and described sequentially, one of ordinary skill will appreciate that some or all of the steps may be executed in different orders, may be combined or omitted, and some or all of the steps may be executed in parallel. Further, in one or more of the example embodiments, one or more of the steps described below may be omitted, repeated, and/or performed in a different order. In addition, a person of ordinary skill in the art will appreciate that additional steps not shown in FIG. 11, may be included in performing this method. Accordingly, the specific arrangement of steps should not be construed as limiting the scope.

Referring now to FIGS. 1-11, the example method 1100 begins at the START step and proceeds to step 1102, where a device (e.g., device 600, device 900) is provided. In certain example embodiments, the device includes multiple magnets (e.g., magnet 410) mounted on at least one mounting surface (e.g., mounting surface 883A, mounting surface 683B, mounting surface 983) of the device. Each magnet can have a first end (e.g., top end 414) and a second end (e.g., bottom end 415), where the first end has a first polarity (e.g., positive polarity), and where the second end has a second polarity (e.g., negative polarity). The first polarity can be opposite the second polarity, which generates a magnetic field (e.g., magnetic field 418) for each magnet.

In step 1104, the device (e.g., device 700, device 800) is placed at a location proximate to the portion of the body. The multiple magnets (e.g., magnet 510A, magnet 510C) generate a plurality of magnetic fields (e.g., magnetic field 518A, magnetic field 518B). In certain example embodiments, if the multiple magnets are placed close enough to each other, the magnetic field generated by one magnet can overlap (intersect) with one or more magnetic fields generated by one or more other magnets. In such a case, the magnetic fields can overlap in a target area (e.g., target area 540), intensifying the effect of the magnetic fields. The portion of the body can be disposed within the target area.

Placing the portion of the body within the target area can cause a "pinching" affect that stimulates the structure and metabolism of subcutaneous tissue and blood, softens cell structure, and causes red blood cells to concentrate in the targeted area. In step 1106, the device from the location proximate to the portion of the body is removed. In certain example embodiments, the device is removed after some period of time (e.g., 3 minutes, 10 minutes, 15 minutes, 45 minutes). The period of time can vary but is used to prevent adverse effects on the portion of the body that can result from excessive exposure to the magnetic fields, particularly in the target area. When step 1106 is complete, the process proceeds to the END step.

The devices, systems, and methods described herein provide for pain relief using multiple magnets oriented in a particular way. Example embodiments allow for effective treatment of a number of conditions of a body (e.g., a human body) by stimulating subcutaneous cellular structure, encouraging increased blood flow to the application area, and relieving inflammation associated with arthritis, stressed muscles, bone/cartilage joint damage, and other maladies. Treatment using example embodiments can be self-administered and can result in a reduction or elimination of one or more of a number of drugs prescribed and/or otherwise administered to treat such conditions.

Example embodiments can be configurable by a user. For example, one or more magnets of an example device can have a mineral core disposed therein, where the mineral core can be removed and/or replaced by a user. The mineral core can alter the magnetic field generated by the magnet. As another example, a magnet of an example device can be set on a plane that is acutely variant from the plane on which one or more other magnets of the example device are set. In such a case, the resulting magnetic fields can intersect with each other and create a target area in which pain relief for a portion of a body can occur.

Example embodiments can have one or more of a number of configurations (e.g., handle, strap) that allow a user increased flexibility as to areas of the body that can be treated. As a result, example embodiments can relieve pain through self-administration for most, if not all, parts of a body.

Although embodiments described herein are made with reference to example embodiments, it should be appreciated by those skilled in the art that various modifications are well within the scope and spirit of this disclosure. Those skilled in the art will appreciate that the example embodiments described herein are not limited to any specifically discussed application and that the embodiments described herein are illustrative and not restrictive. From the description of the example embodiments, equivalents of the elements shown therein will suggest themselves to those skilled in the art, and ways of constructing other embodiments using the present disclosure will suggest themselves to practitioners of the art. Therefore, the scope of the example embodiments is not limited herein.

What is claimed is:

1. A device used for relieving pain, comprising:
   a body comprising at least one mounting surface; and
   at least three magnets disposed on the at least one mounting surface, wherein each magnet has a top end and a bottom end, wherein the top end has a positive polarity, wherein the bottom end has a negative polarity, wherein the positive polarity attracts the negative polarity, wherein the bottom end of each magnet of the at least three magnets is disposed against the at least one mounting surface, wherein none of the at least three magnets has the top end disposed against the at least one mounting surface,
   wherein all of the at least three magnets are distributed substantially equidistantly around a center point of the body, wherein each magnet creates a magnetic field, wherein the magnetic field created by each magnet flows from its own negative polarity to its own positive polarity, wherein the top end of each magnet is tilted toward the center point of the body at an angle relative to the body, and wherein the at least three magnetic fields created by the at least three magnets intersect at a first target area above the center point.

2. The device of claim 1, wherein each magnet of the at least three magnets comprises ferrite oxide.

3. The device of claim 1, wherein each magnet of the at least three magnets comprises a cavity disposed therein.

4. The device of claim 3, further comprising:
   at least one mineral core, wherein the at least one mineral core is disposed in the cavity of at least one of the at least three magnets, wherein the at least one mineral core alters at least one magnetic field of the at least three magnetic fields, and wherein altering the at least one magnetic field alters the first target area.

5. The device of claim 4, wherein the at least one mineral core is different than a composition of each magnet.

6. The device of claim 5, wherein the at least one mineral core is replaceable by a user.

7. The device of claim 5, wherein the at least three magnetic fields further intersect at a second target area, wherein the first target area is disposed above the top end of the at least three magnets, and wherein the second target area is disposed below the bottom end of the at least three magnets.

8. The device of claim 1, further comprising:
   at least one magnet platform disposed on the at least one mounting surface, wherein the at least one magnet platform encases at least one magnet of the at least three magnets, and wherein the at least one magnet platform is coupled to the body.

9. The device of claim 8, wherein the at least one magnet platform comprises at least one cover and at least one base, wherein the at least one cover is removable by a user to access at least one magnet of the at least three magnets.

10. The device of claim 9, wherein the at least one magnet platform comprises at least three magnet platforms, wherein each base of the at least three magnet platforms is antiparallel with a remainder of bases of the at least three magnet platforms.

11. The device of claim 1, wherein the at least one mounting surface comprises at least three mounting surfaces, wherein each mounting surface of the at least three mounting surfaces is antiparallel with a remainder of the at least three mounting surfaces.

12. The device of claim 1, wherein the at least one mounting surface comprises at least three mounting surfaces, wherein the at least three mounting surfaces are distributed substantially equidistantly around the center point, wherein each mounting surface is directed toward the center point at the angle.

13. The device of claim 12, wherein the angle is approximately 4°.

14. The device of claim 1, wherein the first target area is located at a distance from the center point, wherein the first target area corresponds to a location of a human body.

15. The device of claim 4, wherein the at least one mineral core comprises at least one non-mineral component.

16. The device of claim 15, wherein the at least one non-mineral component comprises a naturally-occurring organic material.

17. A method for relieving pain in a portion of a body, the method comprising:
   providing a device, wherein the device comprises at least three magnets mounted on at least one mounting surface of the device, wherein each magnet comprises a top end and a bottom end, wherein the top end has a positive polarity, wherein the bottom end has a negative polarity, and wherein the positive polarity attracts the negative polarity, wherein the at least three magnets are distributed substantially equidistantly around a center point of the body, wherein the bottom end of each magnet of the at least three magnets is disposed against the at least one mounting surface, wherein none of the at least three magnets has the top end disposed against the at least one mounting surface;
   placing the device at a location proximate to the portion of the body, wherein each magnet generates a magnetic field, wherein the magnetic field created by each magnet flows from its own negative polarity to its own positive polarity, wherein the top end of each magnet is tilted toward the center point at an angle relative to the body, wherein the magnetic fields generated by the at least three magnets intersect in a first target area above the center point, and wherein the portion of the body is disposed in the first target area; and
   removing, after a period of time, the device from the location proximate to the portion of the body.

18. The method of claim 17, further comprising:
   inserting, prior to placing the device at the location, a first mineral core into a cavity within each magnet of the at least three magnets, wherein the first mineral core alters the magnetic fields generated by the at least three magnets so that the magnetic fields intersect at a second target area.

\* \* \* \* \*